(12) United States Patent
Rousseau

(10) Patent No.: US 8,973,582 B2
(45) Date of Patent: Mar. 10, 2015

(54) TONGUE SUSPENSION DEVICE AND METHOD

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 183 days.

(21) Appl. No.: 13/307,482

(22) Filed: Nov. 30, 2011

(65) Prior Publication Data

US 2013/0133669 A1   May 30, 2013

(51) Int. Cl.
*A61F 5/56* (2006.01)
*A61C 5/14* (2006.01)

(52) U.S. Cl.
USPC ............................................. 128/848; 128/860

(58) Field of Classification Search
USPC ................. 128/848, 859–862, 207.18; 623/9, 623/23.72; 433/6–7; 600/29–30, 216, 228; 606/231, 230–233, 228
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,192,271 A | 3/1993 | Kalb et al. |
| 5,192,274 A | 3/1993 | Bierman |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |

(Continued)

FOREIGN PATENT DOCUMENTS

| | | |
|---|---|---|
| CN | 2465680 | 12/2001 |
| CN | 201029957 Y | 3/2008 |

(Continued)

OTHER PUBLICATIONS

Cole et al., "Snoring: A Review and a Reassessment", J. of Otolaryngology, vol. 24, No. 5 pp. 303-306 (1995).

(Continued)

*Primary Examiner* — Alireza Nia
*Assistant Examiner* — Ophelia A Hawthorne

(57) ABSTRACT

An implantable tissue suspension device and its method for use. The device includes first and second filamentary elements bonded together only at a central connection region such that first and second leading and trailing legs of the respective first and second filamentary elements extend outwardly from the central connection region. The method includes implanting the device such that the central connection region extends laterally across a patient's tongue and the first and second leading and trailing legs of the first and second filamentary elements extend through the tongue such that ends thereof are positioned external to the genioglossus muscle.

6 Claims, 16 Drawing Sheets

(56) References Cited

U.S. PATENT DOCUMENTS

| | | | |
|---|---|---|---|
| 5,843,077 A | 12/1998 | Edwards | |
| 5,931,855 A | 8/1999 | Buncke | |
| 6,161,541 A | 12/2000 | Woodson | |
| 6,190,401 B1 | 2/2001 | Green et al. | |
| 6,241,747 B1 | 6/2001 | Ruff | |
| 6,250,307 B1 | 6/2001 | Conrad et al. | |
| 6,348,156 B1 | 2/2002 | Vishnoi et al. | |
| 6,431,174 B1 | 8/2002 | Knudson et al. | |
| 6,432,437 B1 | 8/2002 | Hubbard | |
| 6,457,472 B1 | 10/2002 | Schwartz et al. | |
| 6,513,530 B2 | 2/2003 | Knudson et al. | |
| 6,523,542 B2 | 2/2003 | Knudson et al. | |
| 6,578,580 B2 | 6/2003 | Conrad et al. | |
| 6,589,549 B2 | 7/2003 | Shih et al. | |
| 6,599,310 B2 | 7/2003 | Leung et al. | |
| 6,627,600 B2 | 9/2003 | Boutignon | |
| 6,634,362 B2 | 10/2003 | Conrad et al. | |
| 6,638,284 B1 | 10/2003 | Rousseau et al. | |
| 6,716,251 B1 | 4/2004 | Asius et al. | |
| 6,742,524 B2 | 6/2004 | Knudson et al. | |
| 6,755,868 B2 | 6/2004 | Rousseau | |
| 6,800,082 B2 | 10/2004 | Rousseau | |
| 6,899,105 B2 | 5/2005 | Krueger et al. | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,056,331 B2 | 6/2006 | Kaplan et al. | |
| 7,135,189 B2 | 11/2006 | Knapp | |
| 7,146,981 B2 | 12/2006 | Knudson et al. | |
| 7,166,570 B2 | 1/2007 | Hunter et al. | |
| 7,213,599 B2 | 5/2007 | Conrad et al. | |
| 7,237,554 B2 | 7/2007 | Conrad et al. | |
| 7,261,702 B1 | 8/2007 | Alexandre et al. | |
| 7,288,075 B2 | 10/2007 | Parihar et al. | |
| 7,297,102 B2 | 11/2007 | Smith et al. | |
| 7,322,993 B2 | 1/2008 | Metzger et al. | |
| 7,337,781 B2 | 3/2008 | Vassallo | |
| 7,360,432 B2 | 4/2008 | Lehtonen | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,442,389 B2 | 10/2008 | Quelle et al. | |
| 7,601,164 B2 | 10/2009 | Wu | |
| 7,669,603 B2 | 3/2010 | Knudson et al. | |
| 7,806,908 B2 | 10/2010 | Ruff | |
| 7,850,894 B2 | 12/2010 | Lindh, Sr. et al. | |
| 7,857,829 B2 | 12/2010 | Kaplan et al. | |
| 7,888,119 B2 | 2/2011 | Sugaya et al. | |
| 8,142,422 B2 | 3/2012 | Makower et al. | |
| 8,413,661 B2 * | 4/2013 | Rousseau et al. | 128/848 |
| 2001/0037133 A1 | 11/2001 | Knudson et al. | |
| 2002/0144685 A1 | 10/2002 | Ivanovich et al. | |
| 2003/0004579 A1 | 1/2003 | Rousseau et al. | |
| 2003/0034312 A1 | 2/2003 | Unger et al. | |
| 2003/0149445 A1 | 8/2003 | Knudson et al. | |
| 2003/0149447 A1 | 8/2003 | Morency et al. | |
| 2003/0149488 A1 | 8/2003 | Metzger et al. | |
| 2003/0176875 A1 | 9/2003 | Anderson et al. | |
| 2004/0020492 A1 | 2/2004 | Dubrul et al. | |
| 2004/0020498 A1 | 2/2004 | Knudson et al. | |
| 2004/0028676 A1 | 2/2004 | Klein et al. | |
| 2004/0044366 A1 | 3/2004 | Bonutti et al. | |
| 2004/0102796 A1 | 5/2004 | Hill et al. | |
| 2004/0139975 A1 | 7/2004 | Nelson et al. | |
| 2004/0144395 A1 | 7/2004 | Evans et al. | |
| 2004/0147811 A1 | 7/2004 | Diederich et al. | |
| 2004/0149290 A1 | 8/2004 | Nelson et al. | |
| 2004/0153127 A1 | 8/2004 | Gordon et al. | |
| 2004/0231678 A1 | 11/2004 | Fierro | |
| 2005/0038472 A1 | 2/2005 | Furst | |
| 2005/0082452 A1 | 4/2005 | Kirby | |
| 2005/0092334 A1 | 5/2005 | Conrad et al. | |
| 2005/0115572 A1 | 6/2005 | Brooks et al. | |
| 2005/0121039 A1 | 6/2005 | Brooks et al. | |
| 2005/0159637 A9 | 7/2005 | Nelson et al. | |
| 2005/0165352 A1 | 7/2005 | Henry et al. | |
| 2005/0199248 A1 | 9/2005 | Pflueger et al. | |
| 2005/0203576 A1 | 9/2005 | Sulamanidze et al. | |
| 2005/0251255 A1 | 11/2005 | Metzger et al. | |
| 2005/0267321 A1 | 12/2005 | Shadduck | |
| 2005/0267531 A1 | 12/2005 | Ruff et al. | |
| 2005/0267532 A1 | 12/2005 | Wu | |
| 2005/0267571 A1 | 12/2005 | Spence et al. | |
| 2005/0279365 A1 | 12/2005 | Armijo et al. | |
| 2006/0005843 A9 | 1/2006 | Nelson et al. | |
| 2006/0079935 A1 | 4/2006 | Kolster | |
| 2006/0083767 A1 | 4/2006 | Deusch et al. | |
| 2006/0093644 A1 | 5/2006 | Quelle et al. | |
| 2006/0150986 A1 | 7/2006 | Roue et al. | |
| 2006/0185673 A1 | 8/2006 | Critzer et al. | |
| 2006/0206197 A1 | 9/2006 | Morsi | |
| 2006/0207608 A1 | 9/2006 | Hirotsuka et al. | |
| 2006/0207612 A1 | 9/2006 | Jackson et al. | |
| 2006/0228391 A1 | 10/2006 | Seyedin et al. | |
| 2006/0241339 A1 | 10/2006 | Cook et al. | |
| 2006/0266369 A1 | 11/2006 | Atkinson et al. | |
| 2006/0289015 A1 | 12/2006 | Boucher et al. | |
| 2007/0000497 A1 | 1/2007 | Boucher et al. | |
| 2007/0005109 A1 | 1/2007 | Popadiuk et al. | |
| 2007/0005110 A1 | 1/2007 | Collier et al. | |
| 2007/0102004 A1 | 5/2007 | Nelson et al. | |
| 2007/0102010 A1 | 5/2007 | Lemperle et al. | |
| 2007/0110788 A1 | 5/2007 | Hissong et al. | |
| 2007/0119463 A1 | 5/2007 | Nelson et al. | |
| 2007/0123996 A1 | 5/2007 | Sugaya et al. | |
| 2007/0144531 A1 | 6/2007 | Tomas et al. | |
| 2007/0144534 A1 | 6/2007 | Mery et al. | |
| 2007/0144535 A1 | 6/2007 | Hegde et al. | |
| 2007/0190108 A1 | 8/2007 | Datta et al. | |
| 2007/0204866 A1 | 9/2007 | Conrad et al. | |
| 2007/0209665 A1 | 9/2007 | Gillis et al. | |
| 2007/0227545 A1 | 10/2007 | Conrad et al. | |
| 2007/0233276 A1 | 10/2007 | Conrad et al. | |
| 2007/0246052 A1 | 10/2007 | Hegde et al. | |
| 2007/0256693 A1 | 11/2007 | Paraschac et al. | |
| 2007/0257395 A1 | 11/2007 | Lindh et al. | |
| 2007/0261701 A1 | 11/2007 | Sanders | |
| 2007/0267027 A1 | 11/2007 | Nelson et al. | |
| 2007/0270631 A1 | 11/2007 | Nelson et al. | |
| 2007/0272257 A1 | 11/2007 | Nelson et al. | |
| 2007/0288057 A1 | 12/2007 | Kuhnel | |
| 2007/0295338 A1 | 12/2007 | Loomas et al. | |
| 2007/0295340 A1 | 12/2007 | Buscemi | |
| 2008/0023012 A1 | 1/2008 | Dineen et al. | |
| 2008/0035158 A1 | 2/2008 | Pflueger et al. | |
| 2008/0035160 A1 | 2/2008 | Woodson et al. | |
| 2008/0066764 A1 | 3/2008 | Paraschac et al. | |
| 2008/0066765 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 | 4/2008 | Buscemi et al. | |
| 2008/0146868 A1 | 6/2008 | Henri Robert et al. | |
| 2008/0167614 A1 | 7/2008 | Tolkowsky et al. | |
| 2008/0199824 A1 | 8/2008 | Hargadon | |
| 2008/0208265 A1 | 8/2008 | Frazier et al. | |
| 2008/0221684 A1 | 9/2008 | Nelson et al. | |
| 2008/0312688 A1 | 12/2008 | Nawrocki et al. | |
| 2009/0025734 A1 | 1/2009 | Doelling et al. | |
| 2009/0078411 A1 | 3/2009 | Kenison et al. | |
| 2009/0165803 A1 | 7/2009 | Bhat et al. | |
| 2010/0023055 A1 | 1/2010 | Rousseau | |
| 2010/0024830 A1 | 2/2010 | Rousseau et al. | |
| 2010/0030011 A1 | 2/2010 | Weadock et al. | |
| 2010/0037901 A1 | 2/2010 | Rousseau et al. | |
| 2010/0080791 A1 | 4/2010 | Rousseau et al. | |
| 2010/0106246 A1 * | 4/2010 | Rousseau et al. | 623/9 |
| 2010/0108077 A1 * | 5/2010 | Lindh et al. | 128/848 |
| 2010/0132719 A1 * | 6/2010 | Jacobs et al. | 128/848 |
| 2010/0137794 A1 | 6/2010 | Knudson et al. | |
| 2010/0137905 A1 | 6/2010 | Weadock et al. | |
| 2010/0158854 A1 | 6/2010 | Puisais | |
| 2010/0163056 A1 | 7/2010 | Tschopp et al. | |
| 2010/0211184 A1 | 8/2010 | Rousseau et al. | |
| 2010/0234794 A1 | 9/2010 | Weadock et al. | |

(56) References Cited

U.S. PATENT DOCUMENTS

| | | |
|---|---|---|
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1* | 9/2011 | Frank .................... 606/228 |
| 2011/0282386 A1* | 11/2011 | Friedrich et al. ........ 606/228 |
| 2012/0123449 A1 | 5/2012 | Schaller et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 A | 9/2011 |
| DE | 10245076 A1 | 4/2004 |
| EP | 2145587 A2 | 1/2010 |
| EP | 2517633 A1 | 10/2010 |
| EP | 2386252 A1 | 11/2011 |
| FR | 2651113 A1 | 3/1991 |
| JP | 2001145646 | 5/2001 |
| JP | 2003265621 A | 9/2003 |
| RU | 2005447 C1 | 1/1994 |
| SU | 927236 B | 5/1982 |
| SU | 1697792 A1 | 12/1991 |
| WO | WO 97/13465 | 4/1997 |
| WO | WO 99/00058 A1 | 1/1999 |
| WO | WO 00/66050 A1 | 11/2000 |
| WO | WO 01/21107 A1 | 3/2001 |
| WO | WO 03/096928 A1 | 11/2003 |
| WO | WO 2004/016196 A2 | 2/2004 |
| WO | WO 2004/016196 A3 | 2/2004 |
| WO | WO 2004/020492 | 3/2004 |
| WO | WO 2004/021869 A2 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 A1 | 2/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 A2 | 11/2007 |
| WO | WO 2007/132449 A3 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/118913 A1 | 10/2008 |
| WO | WO 2009/023256 A2 | 10/2008 |
| WO | WO 2009/036094 A2 | 2/2009 |
| WO | WO 2010/065341 A2 | 3/2009 |
| WO | WO 2010/065341 A3 | 3/2009 |
| WO | WO 2010/019376 A2 | 2/2010 |
| WO | WO 2010/035303 A1 | 4/2010 |
| WO | 2012/004758 | 1/2012 |
| WO | WO 2012/041205 A1 | 4/2012 |
| WO | WO 2012/064902 A2 | 5/2012 |
| WO | WO 2012/170468 | 12/2012 |

OTHER PUBLICATIONS

Database: WPI Week 198312, Thomson Scientific, London, GB; AN 1983-D9513K XP002693421.
Harries et al., "The Surgical treatment of snoring", J. of Laryngology and Otology, vol. 110, Issue 12 pp. 1105-1106 (1996).
Huang et al., "Biomechanics of snoring", Endeavour, vol. 19(3): pp. 96-100 (1995).
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
Pang, Kenny et al., "Tongue Suspension Suture in Obstructive Sleep Apnea", Operative Techniques in Otolaryngology, vol. 17, No. 4, pp. 252-256 (2006).
Repose Genioglossus Advancement, INFLUENT Medical, www.influ-ent.com, 1 page (2008).
Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).
Schwab et al., "Upper airway and soft tissue changes induced by CPAP in normal subject", Am. J. Respit. Crit. Care Med., vol. 154, No. 4 pp. 1106-1116 (1996).
Schwartz et al., "Effects of electrical stimulation to the soft palate on snoring and obstructive sleep apnea", J. Prosthetic Dentistry, vol. 76 pp. 273-281 (1996).
Shamsuzzaman et al., "Obstructive Sleep Apnea; Implications for Cardiac and Vascular Disease", JAMA vol. 290, No. 14 pp. 1906-1914 (2003).
Teles et al., "Use of Palatal Lift Prosthesis on Patient Submitted to Maxillectomy: A Case Report", Applied Cancer Res. vol. 25(3), pp. 151-154 (2005).
The Advance System, Aspire Medical, Inc. www.aspiremedical.com, 3 pp (2008).
The Pillar Procedure, Restore Medical, Inc. www.restoremedical.com, 2 pp (2008).
Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).
Wassmuth et al., "Cautery-assisted palatal stiffening operation for the treatment of obstructive sleep apnea syndrome", Otolaryngology—Head and Neck Surgery, vol. 123, pp. 55-60 (2000).
Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).
U.S. Appl. No. 13/486,293, filed Jun. 1, 2012.
Notification of Transmittal of the International Search Report and the Written Opinion of the International Search Authority or the Declaration mailed on Feb. 3, 2010 for PCT/US2009/051921; International Filing Date: Jul. 28, 2009.
Notification of Transmittal of the International Search Report and the Written Opinion of the International Search Authority or the Declaration mailed on May 25, 2010 for PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Dec. 29, 2009 for International Patent Application No. PCT/US2009/061455.
International Search Report dated Jan. 21, 2010 for International Patent Application No. PCT/US2009/052110.

(56) References Cited

OTHER PUBLICATIONS

International Search Report dated Apr. 29, 2010 for International Patent Application No. PCT/US2009/065293.
International Search Report dated May 25, 2010 for International Patent Application No. PCT/US2010/023152.
International Search Report dated May 25, 2010 for International Patent Application No. PCT/US2010/025778.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.
U.S. Appl. No. 61/203,758, filed Dec. 29, 2008, Friedman et al.
International Search Report dated May 24, 2013 for International Patent Application No. PCT/US2012/066011.
International Search Report dated Oct. 2, 2013 for International Patent Application No. PCT/US2013/043238.

* cited by examiner

TONGUE SUSPENSION DEVICE AND METHOD

FIELD OF THE INVENTION

The present invention relates generally to the field of medical devices, and more particularly to medical devices adapted to provide tongue suspension to treat sleep apnea conditions.

BACKGROUND

Obstructive sleep apnea (OSA) is a medical condition that is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

In the human body, the air filled space between the nasal cavity and the larynx is referred to as the upper airway. The most critical part of the upper airway associated with sleep disorders is the pharynx. The pharynx has three different anatomical levels. The nasopharynx is the upper portion of the pharynx located in the back of the nasal cavity. The oropharynx is the intermediate portion of the pharynx containing the soft palate, the epiglottis, and the curve at the back of the tongue. The hypopharynx is the lower portion of the pharynx located below the soft tissue of the oropharynx. The oropharynx is the section of the pharynx that is most likely to collapse due to the high prevalence of soft tissue structure, which leaves less space for airflow. The hypopharynx lies below the aperture of the larynx and behind the larynx, and extends to the esophagus.

As is well known to those skilled in the art, the soft palate and the tongue are both flexible structures. The soft palate provides a barrier between the nasal cavity and the mouth. In many instances, the soft palate is longer than necessary and it extends a significant distance between the back of the tongue and the posterior pharyngeal wall.

Although the muscles relax throughout the body during sleep, most of the muscles of the respiratory system remain active. During inhalation, the diaphragm contracts and causes negative pressure to draw air into the nasal cavity and mouth. The air then flows past the pharynx, through the trachea and into the lungs. The negative pressure causes the tissue of the upper airway to deform slightly, which narrows the airway passage. In apneic patients, the soft palate, the tongue, and/or the epiglottis collapse against the posterior pharyngeal wall to block airflow into the trachea. As the airway narrows, airflow through the pharynx becomes turbulent which causes the soft palate to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep. If apnea or hypopnea occurs more than five times per hour, most medical personnel diagnose the individual as having an upper airway resistance problem. Many of these patients exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

When an individual is awake, the back of the tongue and the soft palate maintain their shape and tone due to their respective internal muscles. As a result, the airway through the pharynx remains open and unobstructed. During sleep, however, the muscle tone decreases and the posterior surface of the tongue and the soft palate become more flexible and distensible. Without normal muscle tone to keep their shape and to keep them in place either alone or as a group, the posterior surface of the tongue, the epiglottis, and the soft palate SP tend to easily collapse to block the airway.

One known treatment, commonly referred to as continuous positive airway pressure (CPAP), is currently the "gold standard" for treating OSA and operates by delivering air into a patient's airway through a specially designed nasal mask or pillow. The flow of air creates positive pressure when the patient inhales to keep the airway open. Although CPAP is considered by many to be an effective non-surgical treatment for the alleviation of snoring and obstructive sleep apnea, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Surgical implants have also been used to treat OSA. One such implant system, sold under the name AIRvance by Medtronic, Inc. of Minneapolis, Minn., uses a titanium screw that is inserted into the posterior aspect of the mandible at the floor of the mouth. A loop of suture is passed through the tongue base and attached to the mandibular bone screw. The procedure achieves a suspension or hammock of the tongue base making it less likely for the base of the tongue to prolapse during sleep. Due to the high activity of the tongue during wakefulness, however, the suture component of this device may act as a cutting element within the tongue, causing device trans-location and ultimately a loss of efficacy of the procedure thereby requiring subsequent removal.

Another known tongue suspension device similarly utilizes a bone screw in the mandible, but has the advantage of being adjustable. The device utilizes a flexible shape memory anchor within the tongue that is shaped similar to a grappling hook to engage the tissue within the tongue base. It is placed through a small incision in the sub-mental region and the suture is attached to a spool-like component attached to the mandible. Two to four weeks after healing, a small incision is made under the chin and a screw is turned to tighten the suture, thus pulling the device forward. While the device provides a simplified installation technique from within the sterile space, the anchors suffered from a high rate of device fracture and failure due to loading within the tongue musculature. Additionally, the risk of damage to the teeth or the nerve roots for the teeth is similar in both devices.

U.S. Pat. No. 7,367,340 describes the use of an element that is anchored to the mandible and is capable of applying force within the tongue to prevent the tongue from collapsing during sleep. In the embodiments described, the device consists of an element that is attached to the mandible though drilling of the mandible to provide a rigid point of fixation. The method of attachment produces essentially the same risk to the dental anatomy and nerve structures within the mandible.

A system is disclosed in US 2008/0208265, Frazier, et al., titled "system and method for percutaneous palate remodeling" discloses a looped tether element with one or more regions of an expanded diameter to reduce the risk of cutting through the tongue. This region is created to provide a flexible implant with a fixed expanded region, a balloon region or an in-situ expanding region. This method provides a large bearing surface on limited regions of the fiber. Additionally, this method requires the addition of an element to create the expanded region on the fiber. It is anticipated that this type of device will also be difficult to extract from the tongue tissues after healing has occurred since the portion buried on the tongue base is larger in cross section than the tracks remaining from the trailing ends of the looped tether.

Given the disadvantages described above, there remains a need for a tongue suspension device that provides a high degree of flexibility, a large load bearing surface and the option of multi-point fixation.

SUMMARY OF THE INVENTION

The present invention provides an implantable tissue suspension device including first and second filamentary elements bonded together only at a central connection region such that first and second leading and trailing legs of the respective first and second filamentary elements extend outwardly from the central connection region. In one embodiment, the central connection region is adapted to be implanted laterally within and across a portion of a patient's tongue, with the first and second leading and trailing legs of the respective first and second filamentary elements having a length sufficient to extend through the tongue and into the submental space.

The first and second filamentary elements may be made of a biocompatible, polymeric material, such as polypropylene, Poly(hexafluoropropylene-VDF), ePTFE, or Polyester. In another embodiment, the first and second filamentary elements may be made of an absorbable material, such as polydioxanone or polyglactin. In yet another embodiment, the first and second filamentary elements may be made of a combination of absorbable and non-absorbable materials.

In yet further alternate embodiments, the first and second filamentary elements may be bonded together using ultrasonic welding, compression thermal welding, RF welding, or shrink tube welding, or alternatively may be bonded together using chemical, solvent or adhesive based techniques.

Also provided is a method for treating obstructive sleep apnea including the steps of obtaining an implantable tissue suspension device having first and second filamentary elements bonded together only at a central connection region such that first and second leading and trailing legs of the respective first and second filamentary elements extend outwardly from the central connection region; implanting the central connection region of the tissue suspension device laterally across a patient's tongue; and passing the first and second leading and trailing legs of the first and second filamentary elements through the tongue such that ends thereof are positioned within submental space.

In one embodiment, the free ends of the filamentary elements are attached to a tissue anchor located within the submental tissues.

In an alternate embodiment, the free ends of one filamentary element are attached to a tissue anchor element within the submental space, and the free ends of the second filamentary element are attached to a structure separate from the tissue anchor element.

The first and second filamentary elements may be made of a biocompatible, polymeric material, such as polypropylene, Poly(hexafluoropropylene-VDF), or nylon, or may be made of an absorbable material such as polydioxanone or polyglactin. In yet another embodiment, the first and second filamentary elements are made of a combination of absorbable and non-absorbable materials.

These and other objects, features and advantages of the present invention will be apparent from the following detailed description of illustrative embodiments thereof, which is to be read in connection with the accompanying drawings.

DETAILED DESCRIPTION

Figure 1:
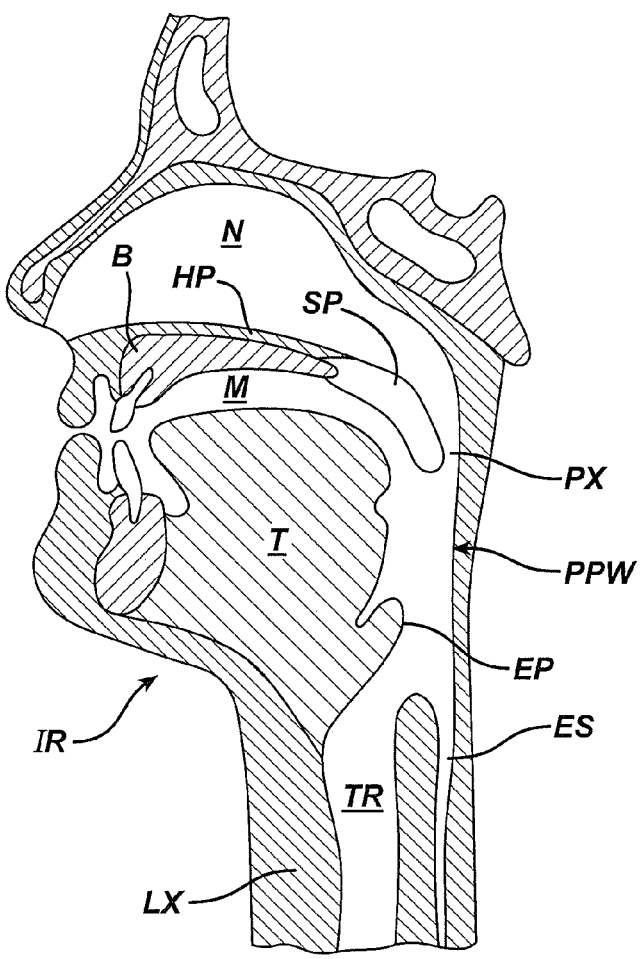
FIGS. 1-3 illustrate the human anatomy.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW. In the human head, an air filled space between the nasal cavity N and the larynx LX is referred to as the upper airway.

Figure 2:
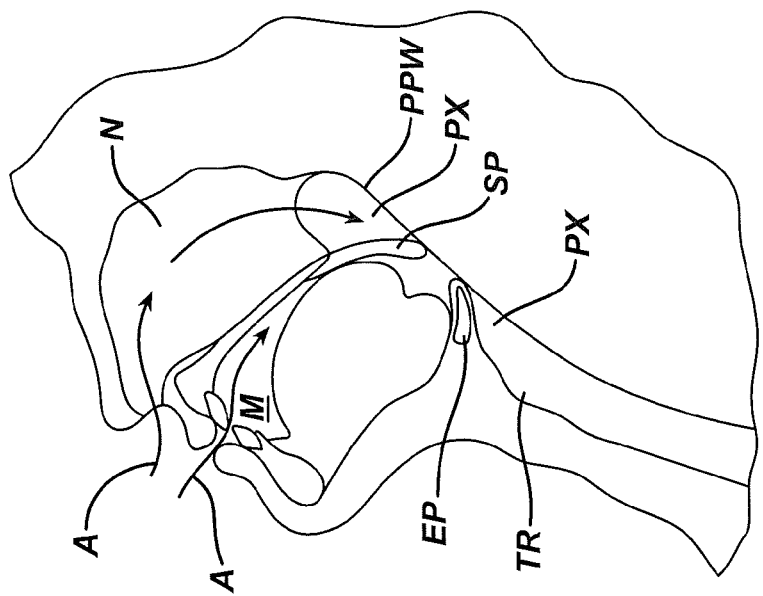

The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating. Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
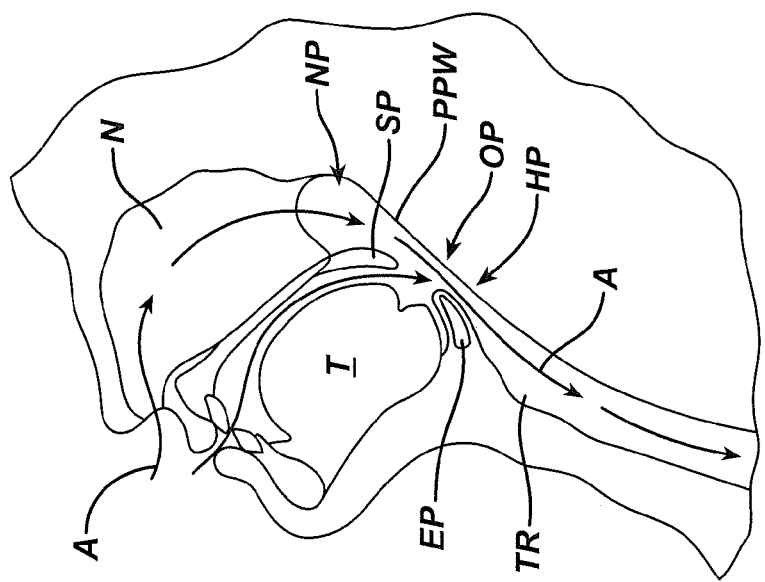

Referring to FIG. 3, without normal muscle tone to keep their shape and to keep them in place either alone or as a group, the posterior surface of the tongue T, the epiglottis EP, and the soft palate SP tend to easily collapse to block the airway A.

It is well known that thermoplastic fibers or filamentary elements can be produced by extrusion and subsequent drawing to increase the straight tensile strength of the material. The draw ratio is a measure of the degree of stretching during orientation of a fiber or filament, and is expressed as the ratio of the cross-sectional area of the undrawn material to that of the drawn material. Typically, the use of higher draw ratios will produce fibers with great axial strength, but the flexibility of the fiber tends to be reduced. In order to produce fibers that have large surface areas for load bearing purposes, the draw ratio is reduced to increase the diameter of the fiber. Although the flexibility of the fiber when compared to high draw ratio fibers of the same diameter may increase as the draw ratio is reduced, elongation of these fibers due to tensile loading increases significantly. As the fiber yield strength is decreased due to reducing the draw ratio, the overall fiber diameter must be increased with low draw fibers to produce materials with similar overall yield force (not stress) for tissue loading without premature yielding. For the purposes of medical implants for tongue suspension, however, it is desirable to produce high yield strength fibers with reduced diameters that can provide a large load bearing surface. Thus, the requirements (high yield strength, low diameter) for an ideal fiber for a medical implant for tongue suspension are conflicting.

The present invention, however, overcomes these limitations and achieves a fiber based medical implant for tongue suspension that has a high degree of flexibility while providing a large load bearing surface in one or more specific locations.

Figure 4:
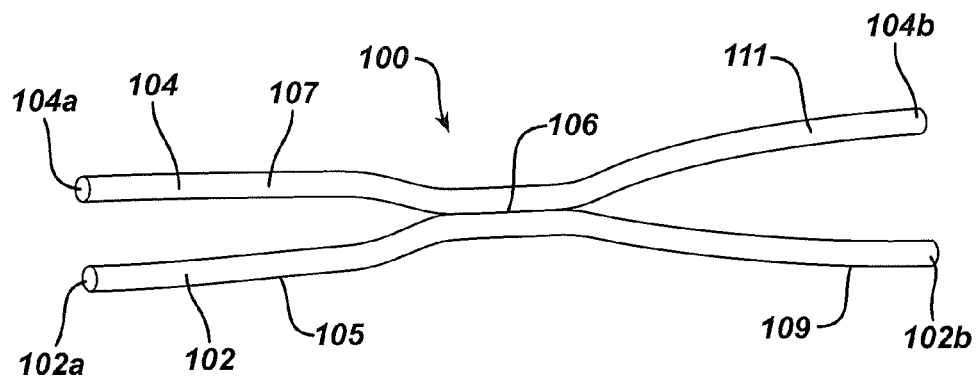
FIG. 4 illustrates an exemplary tissue suspension device according to the present invention.

FIG. 4 illustrates one embodiment of a tissue suspension device 100 according to the present invention. The tissue suspension device 100 includes at least first 102 and second 104 fiber or filamentary (used interchangeably) elements bonded together at one or more discrete connection regions 106. The first and second filamentary elements may be produced as standard solid form extrusions from a variety of biocompatible, polymeric materials, such as non-absorbable thermo-set polymers such as polypropylene, Polyesters, Fluoropolymers, Polyvinylidene fluoride (PVDF), Poly (hexafluoropropylene-VDF) nylon etc. In the embodiments that utilize mechanical connections such as adhesive or crimp type connectors, materials such as rubbers, silicones, urethanes, thermoset polymers and metallic wire may be considered for use, Alternatively, the first and second filamentary elements may be produced through multi-stage extrusion and sintering as is done in the fabrication of ePTFE. In addition, the first and second filamentary elements may be produced from absorbable materials such as polydioxanone, polyglactin etc, or any suitable combination of absorbable and non-absorbable materials. For example, fibers may include absorbable coverings through processing such as coating and co-extrusion. Further, the fibers may have a fully round cross-section, or any suitable non-round cross sectional geometry such as elliptical or rectangular.

Figure 5A:
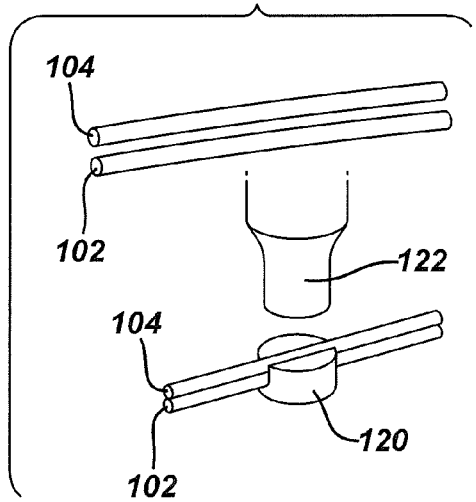
FIGS. 5a and 5b illustrate steps of an exemplary method for producing a device according to the present invention.
Figure 5B:
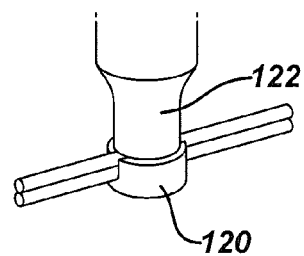

The discrete connection region(s) 106 may be produced through typical bonding methods that are energy based or chemical, mechanical or solvent or adhesive based. For example, FIGS. 5a and 5b illustrate a method of bonding the fibers together through the use of ultrasonic welding. The fibers 104, 102 are placed within a welding nest 120, one on top of the other. An ultrasonic horn 122 is utilized to contact the material and apply vibrational energy to the stacked fibers. In the case of cylindrical fibers, the abutting edges of the cylinders serve as natural energy directors and the vibrational energy is transformed into frictional thermal energy which produces a localized weld without significant damage to the fibers.

Figure 6:
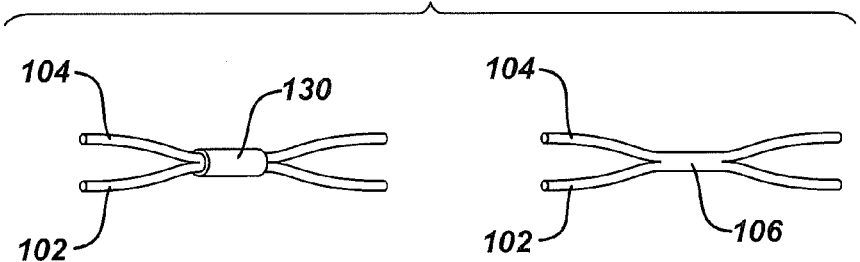
FIG. 6 illustrates an alternate method for producing a device according to the present invention.

Alternatively, the fibers may be subjected to other forms of welding energy including compression thermal welding with heated dies, RF welding to provide very local welding at the interface of the two fibers or shrink tube lap welding. While the first three methods of welding provide welded joints, the use of the shrink tube welding may be preferable as it produces a solid, seamless welded region. Shrink tube welding is depicted in FIG. 6, and includes a shrink tube 130 that has a transition temperature (shrink temperature) that is greater than the melt temperature of the first and second fibers 102, 104. Thus, as the shrink tube collapses/compresses at the transition temperature and exerts a compaction force on the fibers, the molten fiber polymer flows together and effectively welds. The shrink tube is subsequently removed, leaving the welded fibers. Additionally, the shape of the welded zone of material may be adapted to preferred geometries through the use of a non-uniform shrink tube or by confinement of the tube by horizontal compression.

It may also be desirable to produce the tissue supporting device of the present invention through the use of adhesive or solvent along the interface of the first and second fiber in the discrete connection region. The adhesive may be curable/reactive, or it may be of the thermal melt type.

When materials such as ePTFE are used, the discrete connection region(s) is created through the use of volume compaction and re-sintering of the material. ePTFE is formed as an expanded Teflon material with free volume located similar to a foam structure. The material is formed through a paste extrusion and is then subjected to a sintering process to cause bonding of the nodules of material to create a fiber with adequate strength and a high degree of suppleness. With ePTFE, the fiber is placed within compaction dies and is subjected to temperatures similar to those utilized in the sintering process, which enables fusion of the fibers at discrete locations.

Figure 7:
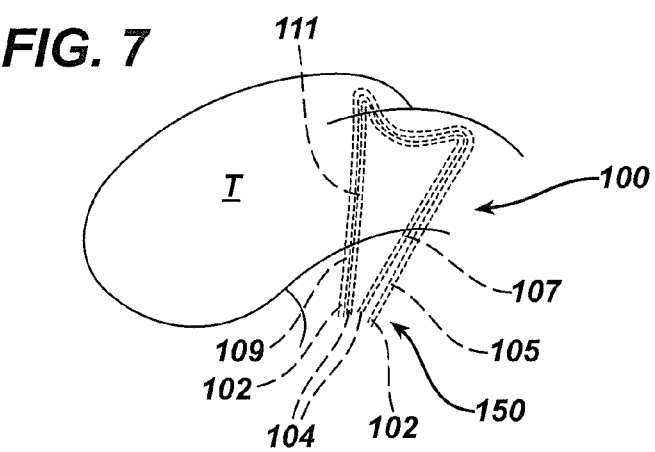
FIGS. 7 and 8 illustrate various anchoring points for the device of the present invention.

Particular applications of the devices of the present invention will now be described in detail with reference to FIGS. 7 and 8. As indicated previously, the devices described herein have particular application for tongue suspension for the treatment of OSA. Referring also back to FIG. 4, the first and second fibers 102, 104 are joined only at one or more discrete connection regions 106. In the illustrated embodiment, the device includes a single discrete connection region centrally located between first 102a, 104a and second 102b, 104b ends of the first and second fibers respectively. As such, there remains a single fiber leading leg 105, 107 and trailing leg 109, 111 for each of the first and second filaments respectively on either side of the discrete connection region. The single fiber leading and trailing legs provide flexibility of typical monofilament fibers as they remain unaltered from the extruded condition. The volume of the combined fibers at the centrally located discrete connection region 106 provides an increased load bearing surface at the center of the tongue which also serves to minimize the risk of pull out. FIG. 7 illustrates the tissue suspension device 100 implanted within the tongue T. The connection region 106 lies along an axis that is substantially perpendicular with an anterior-posterior axis of the tongue. The leading and trailing legs of the first and second fibers 105, 109; 107, 111 preferably extend toward to a substantially common fixation point 150 located within the posterior aspect of the mental tubercle, near the genio hyoid tubercle. The anchor may be either affixed to the soft tissues inferior to the mylohyoid muscle, or may be anchored directly to the mandible, slightly inferior to the genio hyoid tubercle.

Figure 9:
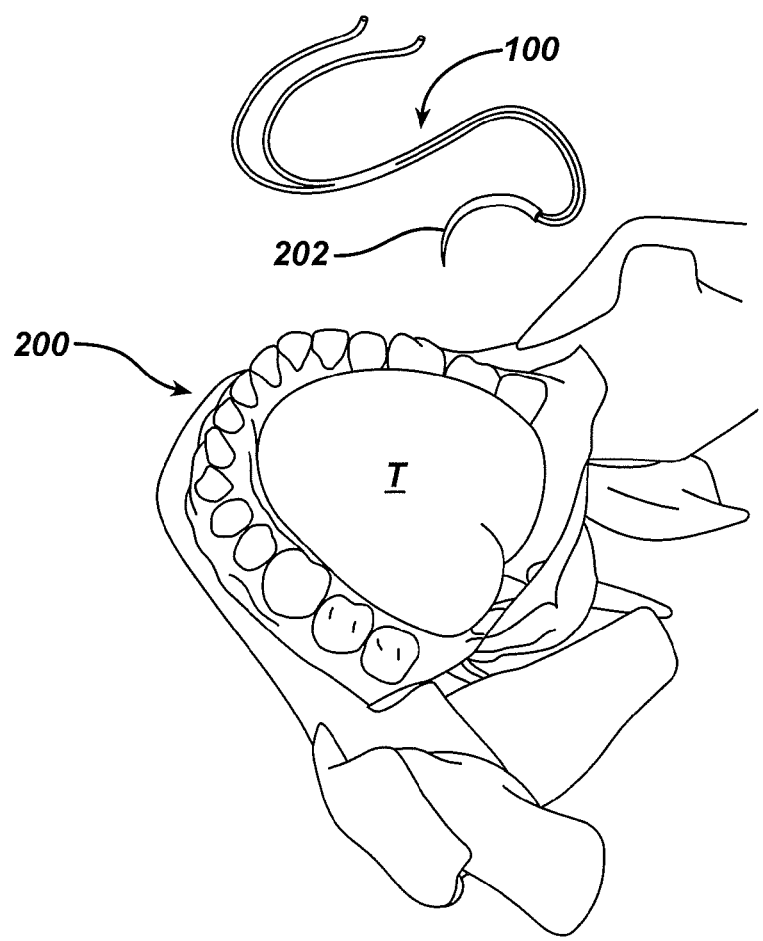
FIGS. 9-20 illustrate steps of exemplary methods for implanting the devices of the present invention.
Figure 10:
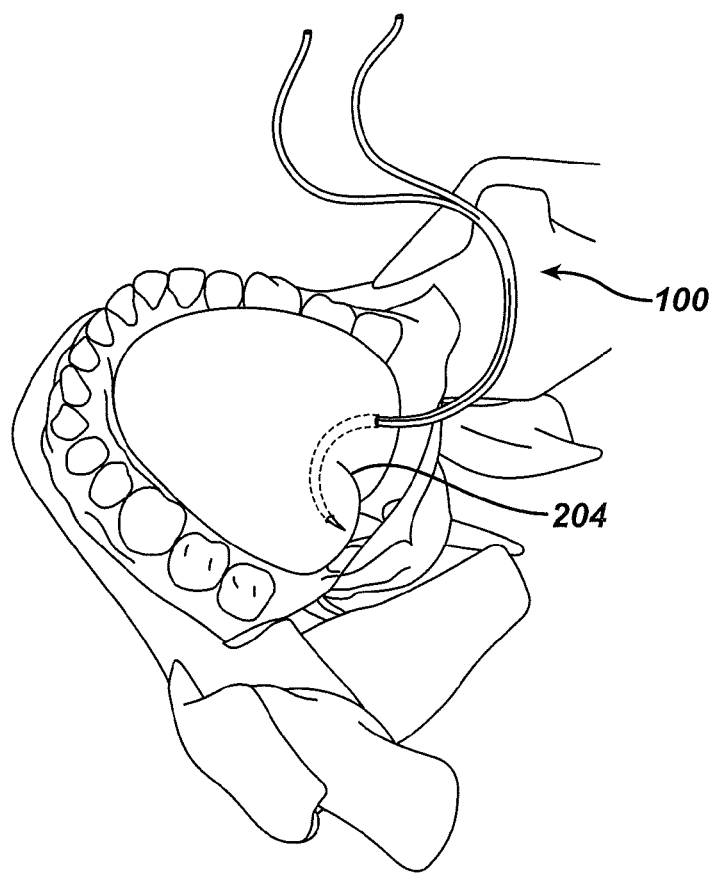
Figure 11:
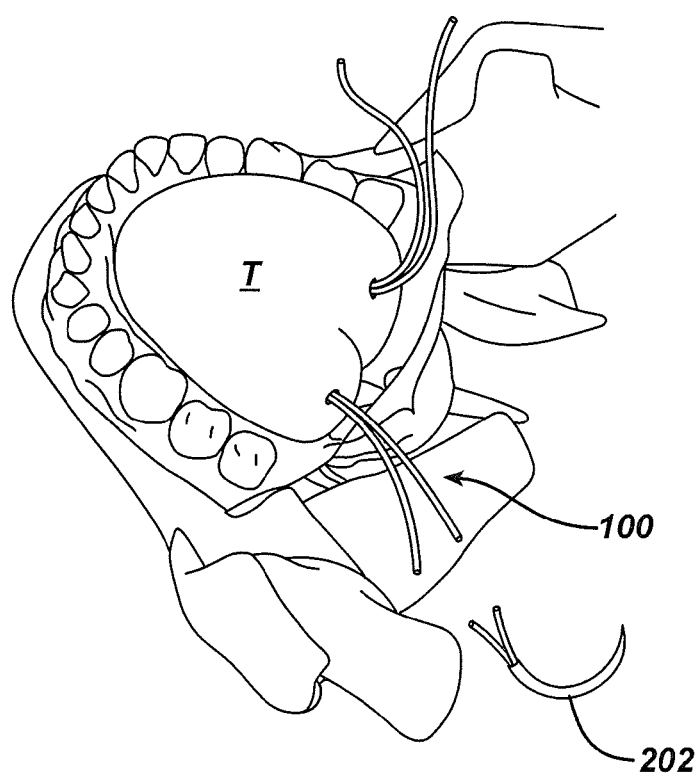
Figure 12:
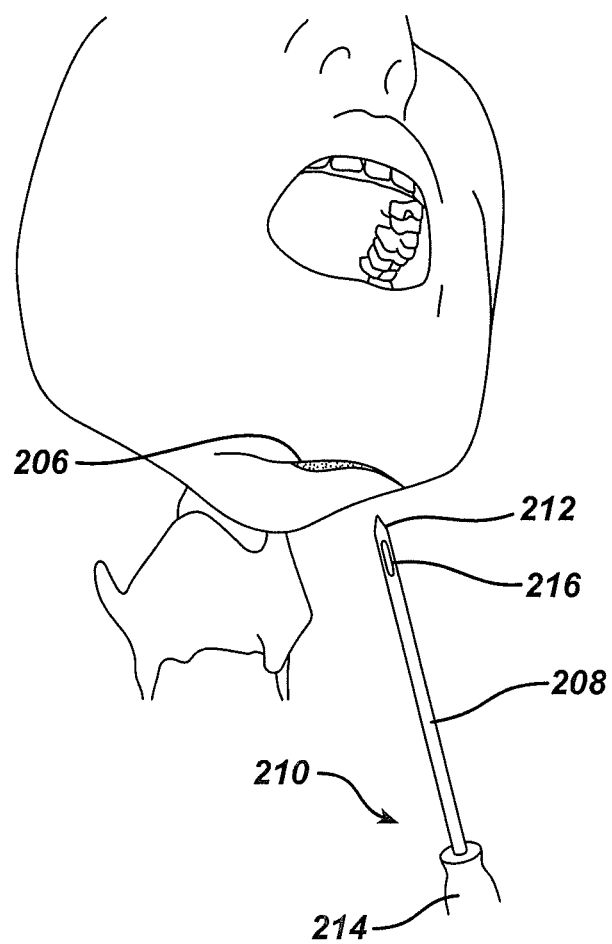
Figure 13:
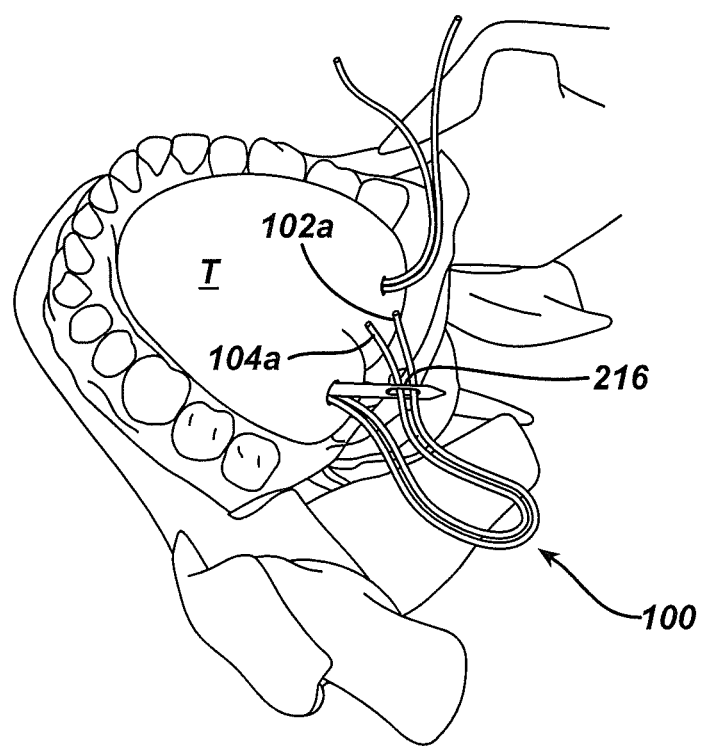

Referring now to FIGS. 9-16, the installation of the fiber element into the tongue with a common fixation point will be described in detail. FIG. 9 provides an illustration of the human mandible 200 in a simplified form to enable clear visualization of the tongue T. The fiber element 100 with the needle 202 attached is provided for passage through the tongue T. Referring to FIG. 10, it can be seen that the needle is passed in a lateral direction with the punctures placed approximately one centimeter from the midline 204 of the tongue. Referring to FIG. 11, the needle 202 is passed entirely through the tongue until the bonded region of the fiber is located within the tissues of the tongue. The needle is then removed either by cutting the fiber or removing any other mechanical connection means that may be employed. As can be seen in FIG. 12, a lateral submental incision 206 is made to expose the musculature. A snare type trocar 210 is then utilized to create a pathway for the fiber to the pass through the tongue from the inferior incision, through the mylohyoid and genioglossus muscles and exiting through the mucosal surface of the tongue within the oral cavity. The snare type trocar consists of a shaft 208 mounted to the handle 214. The shaft is produced with a tapered point 212 to enable passage without cutting the musculature. Additionally, the tip of the trocar preferably is produced with an eyelet feature 216 that is utilized to capture the fiber within the oral cavity.

Figure 14:
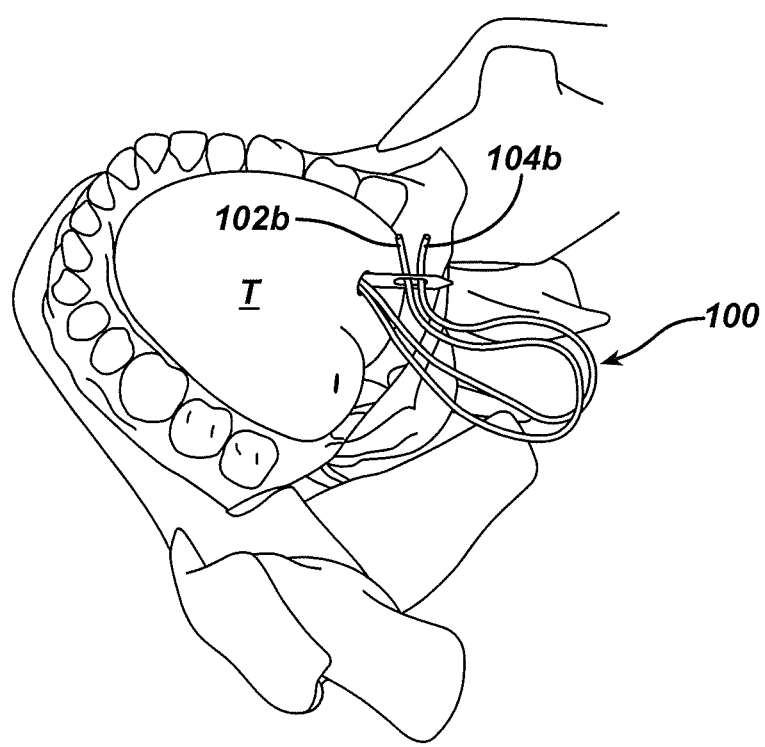
Figure 15:
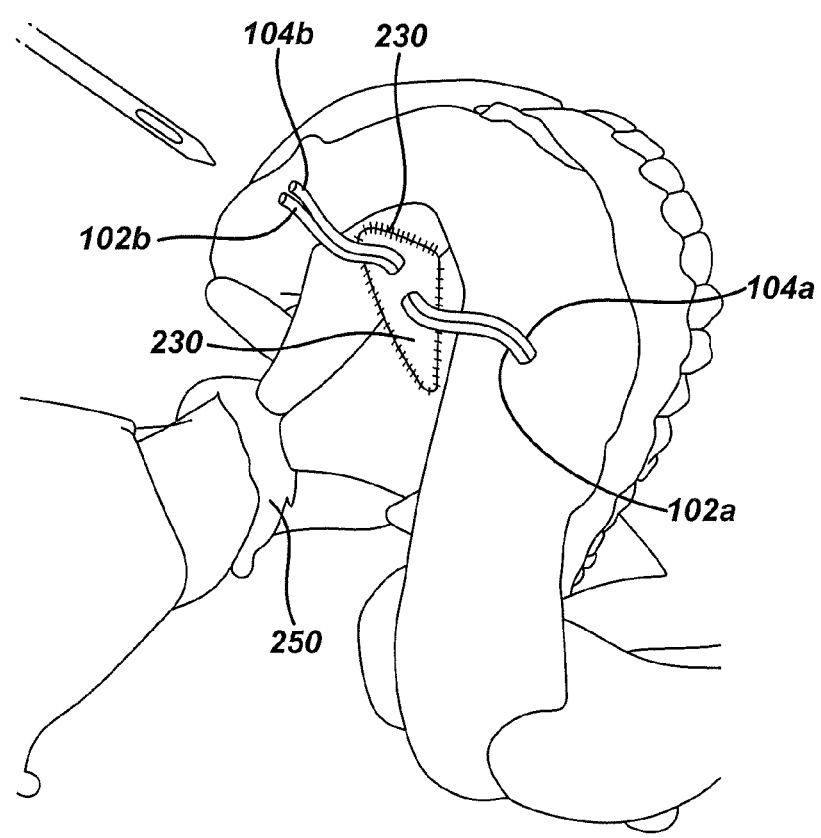
Figure 16:
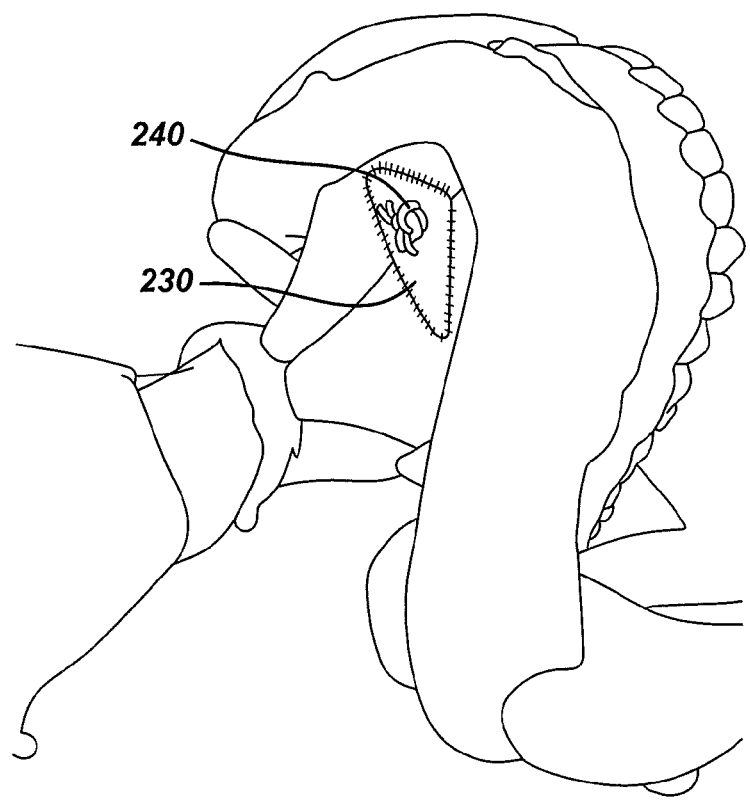

The snare is advanced through the tongue from the submental region to create a tunnel through the tissue. The tip of the snare is guided to the puncture site previously created in the lateral portion of the tongue mucosal surface. The snare tip is forced through the puncture and exits into the oral cavity alongside of the fiber element ends. In the case of the single point of fixation, the two free ends 104a and 102a are threaded through the eyelet portion 216 of the snare. The two ends are then pulled back through the mucosal puncture towards the point of fixation and preferably are passed through the anchor element 230 (FIG. 15). Once the fiber ends from one side have been pulled through the tongue, the snare is advanced again from the submental incision through the tongue into the oral cavity through the second mucosal puncture as is illustrated in FIG. 14. The free ends of the fiber 102b and 104b are threaded through the eyelet and the free ends are again pulled through the mucosal puncture and through the tongue and associated anchor 230 as illustrated in FIG. 15. Tension is applied to the free ends of the fiber to advance the tongue base as is necessary and the free ends of the fiber are either tied in a knot 240, clipped or clamped to the fixation anchor as illustrated in FIG. 16.

Figure 8:
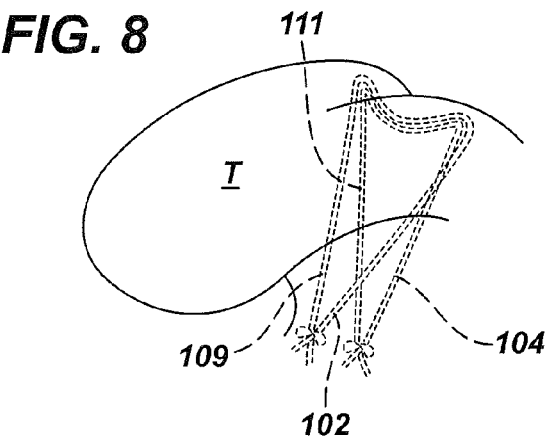
Figure 17:
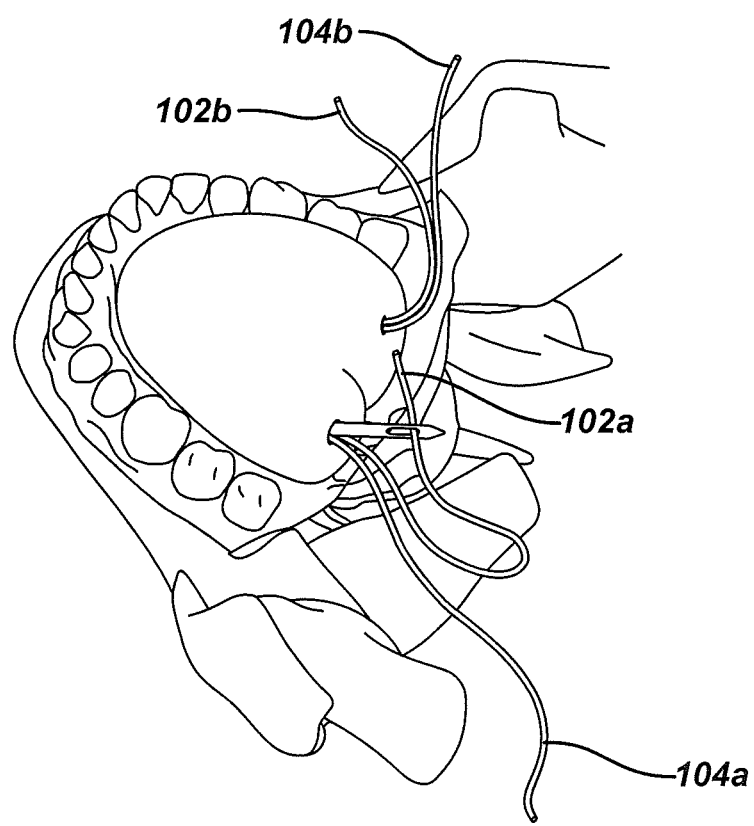
Figure 18:
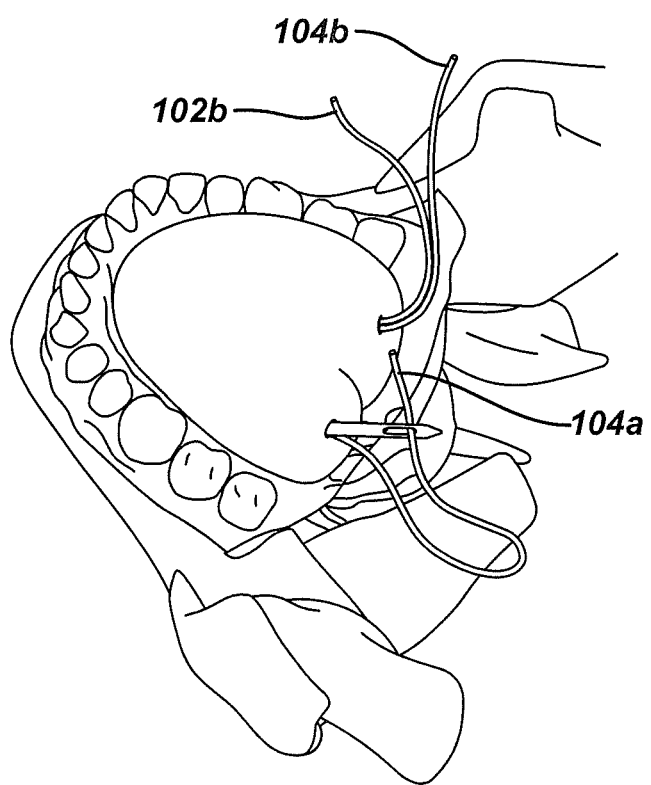
Figure 19:
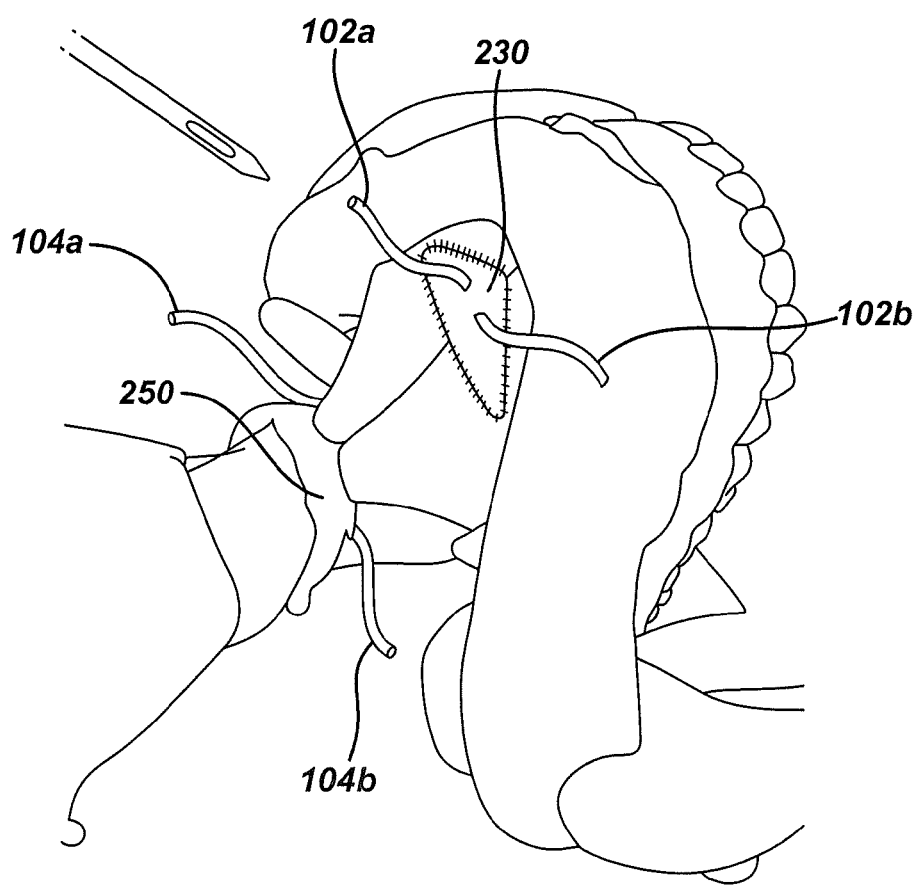

Referring to FIG. 8, the first and second fibers may alternatively be anchored at more than one location or fixation point such as a soft anchor located as previously detailed and the hyoid bone. This enables creation of sling effects that are more stable and resist slippage relative to the location or original placement as the number of degrees of freedom of motion have been reduced. In this embodiment, the fiber is placed as previously described in the lateral passage illustrated in FIGS. 9-11. Incisions are then made in the submental region and also in the tissues that provide direct access to the hyoid bone. A larger submental incision made be created with increased tissue dissection to access the hyoid bone 250 or a separate incision made be made near the hyoid bone. The snare is advanced first from the submental incision near the anchor point and is passed into the oral cavity as previously disclosed through the mucosal punctures as is illustrated in FIG. 17. One free end of the fiber 102a is threaded through the snare and is pulled through the tissue to the anchor in the submental region. The snare is then passed though the tissues of the tongue from an origin point located near the hyoid bone. The tip is guided to the same puncture as was previously utilized for pulling free end 102a. Once the snare is within the oral cavity, the free end 104a is threaded through the eyelet as is shown in FIG. 18, and the free end 104a is pulled through the tissues of the tongue to the exit point near the hyoid bone. The procedure is repeated for free ends 102b and 104b resulting in fiber free end placement as illustrated in FIG. 19.

Figure 20:
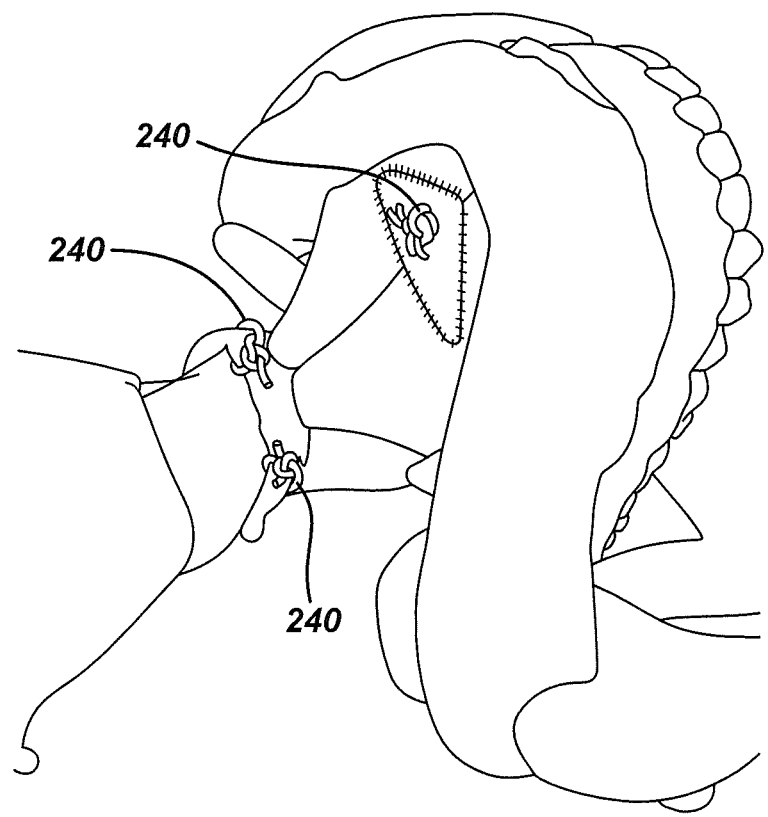

Once the free ends have been passed through the tongue, the free ends 104a and 104b are attached to the hyoid bone either through the use of knots or through the use of bone anchors, hooks, clips, or adhesives. The remaining two free ends 102a and 102b are tensioned and the tongue base and hyoid bone are advanced to the desired position and the two ends are then attached to the anchor device 230. The device may be knotted 240 directly as illustrated in FIG. 20, or alternative fixation devices including bone anchors, hooks, clips, adhesives or the like may be utilized to attach the free ends to the anchor. Unlike the single point of fixation, it can be seen that the tongue base and hyoid bone may be advanced simultaneously and the rotation of the tongue base may be altered favorably.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A method for treating obstructive sleep apnea comprising:
    obtaining an implantable tissue suspension device having first and second filamentary elements each having first and second free ends and a length extending therebetween, said first and second filamentary elements being bonded directly together only at a single discrete connection region centrally located between their respective first and second ends such that a first leading leg of the first filamentary element extends outwardly from a first end of the connection region to the first free end of the first filamentary element, a first trailing leg of the first filamentary element extends outwardly from a second opposite end of the connection region to the second free end of the first filamentary element, a second leading leg of the second filamentary element extends outwardly from the first end of the connection region to the first free end of the second filamentary element, and a second trailing leg of the second filamentary element extends outwardly from the second end of the connection region to the second free end of the second filamentary element;
    implanting the connection region of the tissue suspension device laterally across a patient's tongue; and
    passing the first and second leading and trailing legs of the first and second filamentary elements through the tongue such that the respective free ends of the filamentary elements are positioned external to a genioglossus muscle.

2. The device according to claim 1, wherein the first and second filamentary elements are comprised of a biocompatible, polymeric material.

3. The device according to claim 2, wherein the first and second filamentary elements are comprised of an absorbable material.

4. The device according to claim 3, wherein the first and second filamentary elements are comprised of polydioxanone or polyglactin.

5. The device according to claim 2, wherein the first and second filamentary elements are comprised of a material selected from the group consisting of polypropylene, Poly (hexafluoropropylene-VDF), and nylon.

6. The device according to claim 2, wherein the first and second filamentary elements are comprised of a combination of absorbable and non-absorbable materials.

* * * * *